United States Patent [19]

Frimberger

[11] Patent Number: 4,762,519
[45] Date of Patent: Aug. 9, 1988

[54] APPARATUS FOR PLACING A FEEDING TUBE IN THE STOMACH OF THE HUMAN OR ANIMAL BODY

[75] Inventor: Eckart Frimberger, Munich, Fed. Rep. of Germany

[73] Assignee: Erintrud Frimberger, Kempten, Fed. Rep. of Germany

[21] Appl. No.: 86,562

[22] Filed: Aug. 18, 1987

[30] Foreign Application Priority Data

Aug. 18, 1986 [DE] Fed. Rep. of Germany ....... 3628006

[51] Int. Cl.⁴ .......................................... A61M 25/00
[52] U.S. Cl. ..................... 604/280; 604/270
[58] Field of Search ............. 604/280, 270, 51–53, 604/164; 128/328, 320

[56] References Cited

U.S. PATENT DOCUMENTS 480,870  8/1892  Harris .................................. 128/320
4,636,199 1/1987 Victor ................................. 604/164

FOREIGN PATENT DOCUMENTS 1139442  2/1985  U.S.S.R. ............................... 604/280

Primary Examiner—Stephen C. Pellegrino
Attorney, Agent, or Firm—Scully, Scott, Murphy & Presser

[57] ABSTRACT

An apparatus, for placing a feeding tube in the stomach of the human or animal body, has:
a hollow needle, which is surrounded by a sleeve, for providing an opening in the abdominal wall and the stomach wall and for bringing the sleeve into the opening:
the tube, which has a first draw member at its one end:
and a thread-like second draw member, which may be introduced through the sleeve, for drawing the tube from the cavity of the stomach into the opening. The connection between the first and the second draw members can be produced inside the stomach. This is achieved in that the second draw member has an expandable loop at its inner end and the first draw member has a coupling element which may pass through the loop and be held fast by contraction of the loop.

19 Claims, 3 Drawing Sheets

APPARATUS FOR PLACING A FEEDING TUBE IN THE STOMACH OF THE HUMAN OR ANIMAL BODY

BACKGROUND OF THE INVENTION

Field of the Invention

The invention relates to an apparatus for placing a feeding tube in the stomach of a human or animal body.

In the case of patients with whom feeding through the oesophagus is not possible, for example as a result of dysphagia after apoplexy or in the case of an oesophageal tumour, feeding can take place by way of a so-called fistula which leads straight into the stomach from the abdominal surface. The present invention is concerned with the improvement of such devices.

Description of the Prior Art

Earlier, such fistulae were established by the surgeon operatively (gastric fistula); nowadays, they can be placed in the form of feeding tubes, more simply, endoscopically. In this connection, the procedure is as follows:

A flexible gastroscope is introduced into the stomach and, under endoscopic control, a hollow needle, upon which a plastic sleeve is arranged, is inserted into the stomach from outside. The hollow needle is subsequently drawn out of the sleeve whilst the sleeve remains in the puncture.

The next step consists in introducing a thread through the sleeve into the stomach, which thread is then gripped from the inside by means of a gripping tool, introduced by way of the endoscopic instrumentation channel, and is drawn out of the body, in which case it is necessary to draw out the gastroscope as well in order to be able to draw the free end of the thread out of the instrumentation channel. This extracorporeal end of the thread is then secured to the tip of the feeding tube outside the body of the patient.

By drawing the end of the thread on the fistula side, the tube is then drawn by way of the mouth and the oesophagus, in the first instance, into the stomach and then into the puncture, in which case the sleeve is drawn, or pushed, at the same time out of the stomach wall and the abdominal wall. The end position of the tube is defined by an annular limiting part on its periphery, owing to the fact that the limiting part reaches the inner wall of the stomach and thus prevents the tube from being drawn through. After the thread has been detached from the now protruding end of the tube and this end has been cut to a desired length, feeding can take place through the tube. The fixing of this tube end may be achieved by means of a plaster.

This known apparatus requires considerable input, in terms of treatment and time, for placing the tube. This is largely because the connection between the thread and the tube can only be produced outside the body, and thus, as described previously, the withdrawal of the thread by means of the gastroscope is necessary.

SUMMARY OF THE INVENTION

The invention provides an apparatus in which a part for insertion through the mouth and oesophagus into the stomach is provided and may be gripped, within the stomach, by a loop of, for example thread inserted through the abdominal wall.

The underlying object of the invention is to develop an apparatus of the general type mentioned above, in such a way that the connection between the thread-like draw element and the tube, for insertion through the mouth, can be produced inside the stomach.

In the development according to the invention, first and second thread-like draw members, which are coordinated with the tube and a hollow needle, for insertion through the abdominal wall, are provided with coupling members, which can be connected with each other under endoscopic control, easily and simply, in the stomach. The coupling member coordinated with the hollow needle is, in this connection, formed by means of an expandable loop, whereby the connection can be realized not only easily, but whereby it is also possible in a simple manner to introduce this draw member through the sleeve or preferably the hollow needle. Several developments are possible for the coupling member of the other draw member, e.g. in the form of a hook of a head-like thickened portion. What is essential is that this coupling member can be gripped by the loop.

On account of the reduced input in terms of treatment, when using the apparatus according to the invention there results, for both the person who is administering the treatment and for the patient, treatment which is considerably more pleasant.

The expandable loop may be formed by measures, known per se for the purpose of producing a loop which opens automatically. For example, one side of the loop may be under a tension which acts to separate it from the other side, or the loop may be expanded by a relative displacement of the sides.

Preferably, for particular simplicity, the first draw member, associated with the tube, is formed by a simple wire section, preferably made of metal. This simple wire section automatically forms an effective coupling member when it is inserted through the loop and the loop is subsequently drawn out of the hollow needle. The wire section thereby strikes either against the tip of the hollow needle or against the sleeve and is thereby bent over, in which case an effective coupling element is automatically formed.

The length of the first draw member is preferably greater than the length from the stomach to the mouth of the patient, making it possible to arrange the tube and its draw member outside the gastroscope. For the purposes of arrangement in, or introduction through, the gastroscope, conventional gastroscopes are not suitable when conventional apparatus is used.

The first draw member may be bent or folded, in the region of its inner end, into a Z-shape, to make it possible, despite the course of the wire section at the periphery of the gastroscope, to displace the free end of the wire section longitudinally through an instrument of the gastroscope. It is also possible to achieve this longitudinal displacement by drawing the draw member from outside.

For structural and hygienic reasons, it is advantageous to pack the tube, which may have a cone at its end, and which together with at least a part of the first draw member may form a prefabricated device, in a sterile wrapping. It is possible to open the sterile packing before it is passed through the mouth space, or delay doing so until it is in the cavity of the stomach. In the latter case, the packing material can be removed out of the body, after the tube has been placed, by means of the gastroscope.

It is possible within the scope of the invention to arrange the hollow needle and the loop, which may be introduced through it into the cavity of the stomach, in the form of a prefabricated constructional unit which can be packed, preferably, in a sterile manner. It is advantageous to arrange the loop inside the hollow needle, in such a way that it is ready for use.

A covering cap may be provided, to effectively seal and protect the opening from the outside.

The tube can then be guided out through the covering cap so that when feeding through the tube, it is not necessary to remove the cap.

The cap can be advantageously be secured, in a simple manner, by means of a clamping apparatus acting between the tube and the cap, whereby the tube as a whole is fixed, because its annular limiting part rests against the inner wall of the stomach.

The cap may have a groove, to receive the tube, in which the tube may be clamped. Further, the whole end region of the tube projecting from the cap may be received in the groove. Such an arrangement helps to avoid disturbance of the protuding end of the tube.

Arranged on the tube there may be a flange which, when the tube is placed inside the patient, rests against the inside of the stomach wall in order to avoid the feeding tube slipping out through the stomach wall during the feeding manipulation. If the patient is fed in such a way that the food is pumped into the stomach, the feeding tube ends at the inner end of the flange on the stomach side or the tube extends, with an inner tube part, a few centimetres from the flange into the stomach.

In the case of invalids with an impaired swallowing action, e.g. after a stroke, it may be decided not to pass food into the stomach, as it can pass back into the oesophagus, as a result of the contractions of the stomach, and from there into the bronchial system, with the risk of pneumonia. In order to avoid this complication, the aim is not to let the inner tube part end in the stomach, but to place it as far as possible into the small intestine, as with the distance the risk of the backflow of food out of the small intestine in the direction of the stomach, oesophagus and lung is reduced. In order to make it possible to place of an inner tube part, which is approximately 20 to 30 cm long, in the small intestine, the inner tube part is formed in a loop, the distal end of which is detachably secured to the flange.

DESCRIPTION OF THE PREFERRED EMBODIMENT

Figure 1:
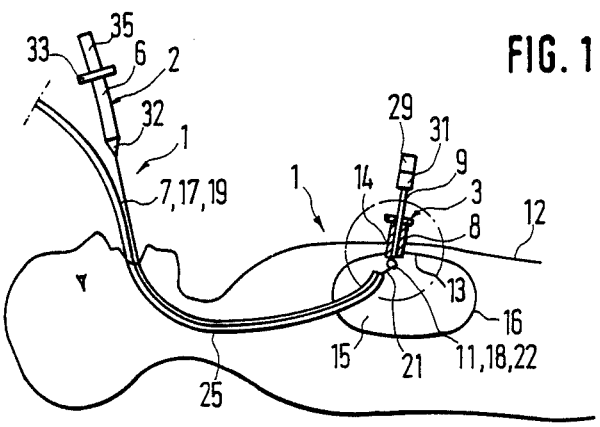
FIG. 1 shows an apparatus embodying the invention, in use.

As can be inferred from FIG. 1, a preferred embodiment of the apparatus, generally denoted with 1, consists of two apparatus parts 2, 3, which are packed in a sterile manner, the packing of the first apparatus part 2 being denoted 4. The first apparatus part 2 includes the feeding tube 6, as well as a connecting part 7, and the second apparatus part 3 has a hollow needle 9, which is surrounded by a sleeve 8, with a second connecting part 11.

The apparatus 1 serves to provide an opening 14 in the abdominal wall 12 and in the stomach wall 13 facing it, and to insert the tube 6 into the opening 14 from the inside, i.e. through the mouth space, the oesophagus and the cavity 15 of the stomach 16.

Both previously described connecting parts 7, 11 are thread- or wire-like draw members 17, 18, of which the draw member 17, which is associated with the tube 6, is formed by a flexible wire 19, which is initially straight, and which is dimensioned so that it is longer than the distance between the cavity 15 of the stomach 16 and the mouth of the patient, so that the tube 6 is located outside the body when the inner end 21 of the draw member 17 is in position ready for coupling or connection.

The draw member 18 associated with the hollow needle 9 is a loop 22 of wire which may be pushed out of a position, in which it is drawn in the hollow needle 9, into the cavity 15 of the stomach 16 and which thereby opens automatically. The latter can be accomplished owing to the fact that only one of the sides 23, 24 of the loop 22, which sides are connected with each other at the loop tip, is displaced. It is also possible to provide both sides 23, 24 with a tension which bends them away from each other, whereby, likewise, automatic opening of the loop 22 is achieved when the latter is pushed out of the hollow needle 9.

In order to insert the tube 6, in the first instance the introducing element 25 of a gastroscope, which is not shown in detail, is introduced into the cavity 15 of the stomach 16 through the mouth of the patient. The connecting part 7 or the draw member 17 of the tube 6, which part or member extends in the longitudinal direction at the edge of the introducing element 25, is introduced with the introducing element 25. The draw member 17 is bent at the inner end of the introducing element 25 in the shape of a Z, i.e. it extends with a bent-in section, 26, into the instrumentation channel, of the introducing element 25 (not shown) and then back from a fold point 27 out in the direction of the stomach 16, in which case the inner end 21 of the draw member 17 can be displaced by means of a push member (not shown), which may be displaced in the instrumentation channel, out of a position in which it is inside the instrumentation channel into a position in which it protrudes out of the instrumentation channel.

Figure 2:
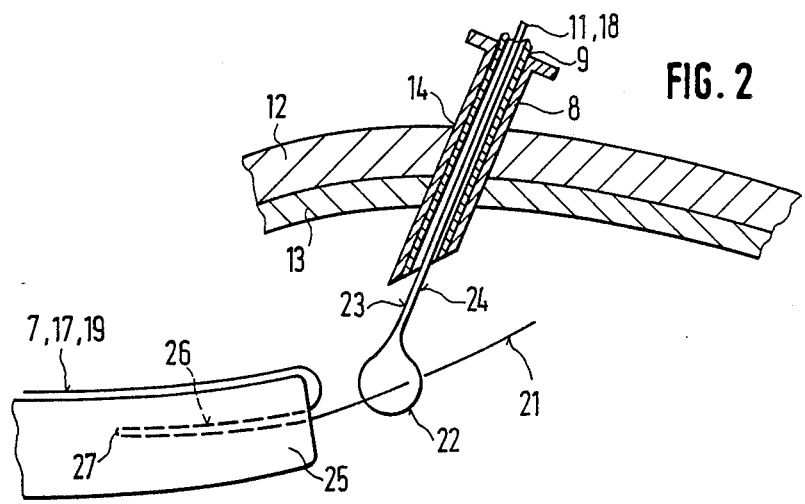
FIG. 2 shows, on a larger scale, the region indicated X in FIG. 1.
Figure 3:
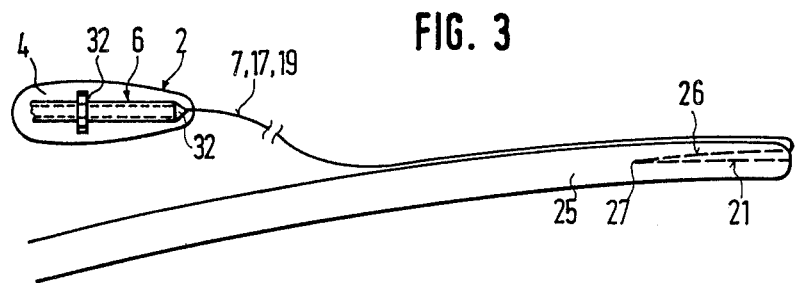
FIGS. 3 to 6 are views, corresponding to FIG. 2, of the apparatus during different stages of treatment.
Figure 4:
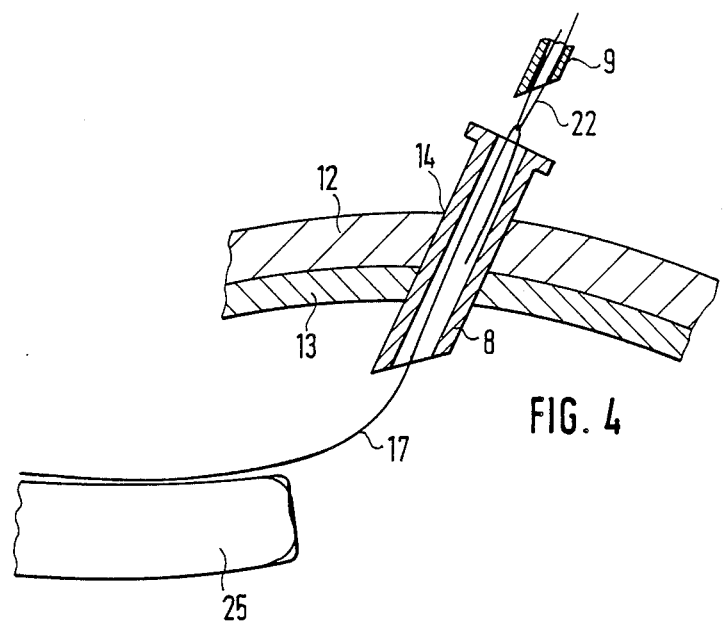

FIG. 2 shows the inner end 21 of the draw member 17 in the pushed-out position in which the inner end 21 is inserted through the loop 22 for connection therewith. When the loop 22 is drawn back out of this position, either on its own or, if applicable, with the hollow needle 9, with the sleeve 8 remaining in the opening 14, the inner end 21 of the draw member 17 is bent in the shape of a hook on account of the impact against the hollow needle 9 or the sleeve 8, whereby a reliable coupling is produced (FIG. 4). After removal of the introducing element 25, the tube 6 is drawn through the mouth, the oesphagus and the cavity 15 of the stomach 16 into the opening 14, by further drawing the loop 22 or the hollow needle 9, the grips of which are represented in a simplified manner and are denoted by 29, 31. The introduction of the tube 6 is facilitated by the presence of a cone 32 at the end thereof.

Figure 5:
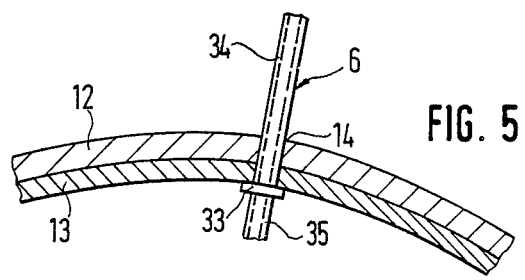

In the position in which it is drawn into the opening 14, the tube 6 occupies the position shown in FIG. 5, in which a flange 33, projecting on the periphery, rests against the inside of the stomach wall 13. The sleeve 8 is pushed out when the tube 6 is drawn into the opening 14. It may now be necessary to cut off the end 34 of the tube 6 protruding from the abdominal wall 12 in order to make the latter the desired length. Feeding can now take place through the tube 6, in which case supply parts, which are not represented, can be fitted to the end 34 of the tube 6 in a known way.

Figure 7:
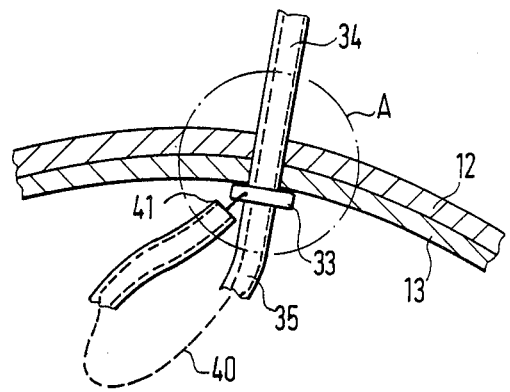
FIG. 7 is a view corresponding to FIG. 5 with inner tube part formed in a loop.
Figure 8:
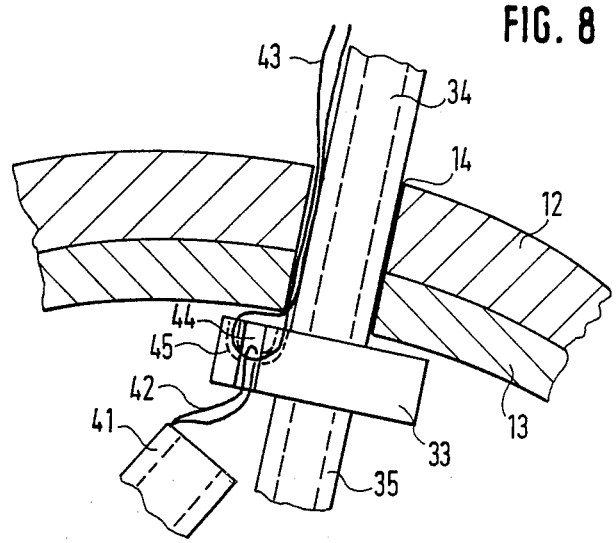
FIG. 8 is an enlarged view of the area A in FIG. 7.

The construction of the feeding tube 6 according to FIGS. 7 and 8 facilitates the insertion of the inner tube part 35 into the small intestine of the patient, which area is not represented and is connected to the stomach 16.

When inserting the feeding tube 6, as described in conjunction with FIGS. 1 to 6, the inner tube part 35 comes to lie in the stomach 16. If, for the placement of the inner tube part 35 into the small intestine, a greater length of the tube part of, for example, 20 to 30 cm, is required, this extended inner tube part 35 after placement comes to lie in the oesophagus of the patient. There this end would have to be gripped with the endoscope and transported into the small intestine.

For this purpose, the endoscope must be extracted and the inner tube end must be gripped and brought into the small intestine through renewed introduction of the endoscope. In order to avoid the extraction and renewed introduction of the endoscope, the inner tube end 35 is formed in a loop 40, as shown in FIG. 7, and its inner end 41 is detachably secured through suitable means, represented, for example, in FIG. 8, to the flange 33. These means can, for example, be formed from, in each case, a thread loop 42, 43 arranged on the end 41 and on the flange 33. The thread loop 42 at the tube end 41 projects into a slot 44 in the flange 33 and is held by the loop 43 which runs through openings 45 transverse to the slot 44. The loop 43 is secured with its ends in the region of the cone 32 or to the draw member 17. The loop 43 is cut off with the described cutting to length of the outer tube part 34, and the thread forming the loop 43 can be drawn out, releasing the loop 42 and with it the inner end 41 of the tube part 35, so that this end can be gripped with the aid of the endoscope and placed into the small intestine.

Figure 6:
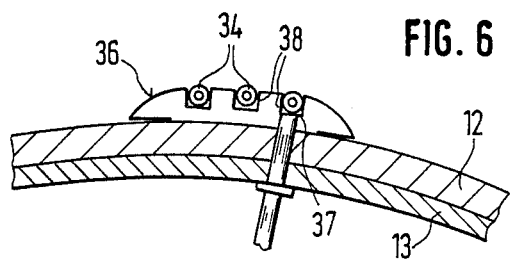

It is advantageous to seal the opening 14 from the outside by means of a covering cap 36 which has a hole 37 through which the end 34 of the tube 6 is guided. The cross section of the hole 37 can be dimensioned so that it is slightly smaller than the cross section of the tube 6, in order that the covering cap 36 sits on the tube 6 with a certain clamping action, whereby there is obtained not only a seal at the edge of the hole 37, but also a mounting support with which the covering cap is held on the outside of the abdominal wall 12. Preferably arranged in the outside of the covering cap 36 are groove-like recesses 38 leading from the hole 37, and extending in a winding manner and being of such a length that the whole end 34 of the tube 6 can be laid therein, as shown in FIG. 6.

The tube 6, and preferably also the covering cap 36, are made of a plastics material compatible with tissue, the cone 32 being pre-formed on the tube 6 in one piece. The draw members 17, 18 are made of a wire of corrosion-resistant metal. It is also possible to manufacture the loop 22 from a plastic wire or band, because such a material is also suitable. However, preferably a metal wire which is indeed flexible, yet has a certain flexural strength, is advantageous for the draw member 17 so that the inner end 21 puts up a resisting force to bending upwards.

The packing 4 can be removed either by hand before the tube 6 is introduced into the digestive tract, or by means of the gastroscope when in the stomach.

What is claimed is:

1. Apparatus for placing a feeding tube in the stomach of the human or animal body, comprising: a hollow needle, surrounded by a sleeve, for providing an opening in the abdominal wall and the stomach wall and for bringing the sleeve into the opening; the tube, which has a first draw member at its one end; and a thread-like second draw member, which may be introduced through the sleeve, for drawing the tube from the cavity of the stomach into the opening, the second draw member having an expandable loop at its inner end and the first draw member having a coupling element which may pass through the loop and be held fast by contraction of the loop.

2. Apparatus according to claim 1, wherein at least one side of the loop is under a tension which seeks to move it away from the other side.

3. Apparatus according to claim 1, wherein the loop may be expanded by a relative displacement of its sides.

4. Apparatus according to claim 1, wherein the first draw member, associated with the tube, is formed from a wire, preferably of metal.

5. Apparatus according to claim 1, wherein the length of the first draw member is greater than the distance between the cavity of the stomach and the mouth of the patient to be treated.

6. Apparatus according to claim 5, wherein the first draw member is bent or folded in the region of its inner end in the shape of a Z.

7. Apparatus according to claim 1, wherein the tube and at least a part of the first draw member form a first prefabricated apparatus part.

8. Apparatus according to claim 7, wherein the first prefabricated apparatus part is packed in a sterile wrapping.

9. Apparatus according to claim 1, wherein the hollow needle and the second draw member form a second prefabricated apparatus part.

10. Apparatus according to claim 9, wherein the second prefabricated apparatus part is packed in a sterile wrapping.

11. Apparatus according to claim 1, wherein a covering cap, for covering the opening on the outside, is associated with said apparatus.

12. Apparatus according to claim 11, wherein a hole, through which the tube may be passed, is arranged in the covering cap.

13. Apparatus according to claim 11, further including a clamping device for securing the tube to the covering cap in a clamping manner.

14. Apparatus according to claim 11, wherein the covering cap has, on its exterior, a groove-like recess for receiving the tube.

15. Apparatus according to claim 14, wherein the tube may be clamped in the recess.

16. Apparatus according to claim 14, wherein the whole end of the tube protruding from the covering cap may be inserted in the groove-like recess.

17. Apparatus according to claim 1, wherein arranged on the tube is a flange which, when the tube is placed inside the patient, abuts against the inside of the stomach wall.

18. Apparatus according to claim 17, wherein the tube includes an inner part, which remains inside the stomach when the flange abuts against the stomach wall, the inner part forming a loop, and the end thereof remote from the flange being detachably secured to the flange.

19. Apparatus according to claim 1, wherein the tube has a cone at its end, to ease insertion.

* * * * *